(12) United States Patent
Gill et al.

(10) Patent No.: US 10,285,798 B2
(45) Date of Patent: May 14, 2019

(54) ESOPHAGEAL STENT

(75) Inventors: Darla Gill, Salt Lake City, UT (US);
Zeke Eller, Dallas, TX (US); Rich Snider, Dallas, TX (US)

(73) Assignee: MERIT MEDICAL SYSTEMS, INC., South Jordan, UT (US)

( * ) Notice: Subject to any disclaimer, the term of this patent is extended or adjusted under 35 U.S.C. 154(b) by 0 days.

(21) Appl. No.: 13/153,150

(22) Filed: Jun. 3, 2011

(65) Prior Publication Data

US 2012/0310363 A1    Dec. 6, 2012

(51) Int. Cl.
*A61F 2/04* (2013.01)
*A61F 2/07* (2013.01)
*A61F 2/95* (2013.01)
*A61F 2/915* (2013.01)

(52) U.S. Cl.
CPC ............ *A61F 2/07* (2013.01); *A61F 2/915* (2013.01); *A61F 2002/044* (2013.01); *A61F 2002/91575* (2013.01); *A61F 2002/9534* (2013.01); *A61F 2220/0075* (2013.01); *A61F 2230/0045* (2013.01); *A61F 2230/0054* (2013.01); *A61F 2230/0078* (2013.01); *A61F 2250/0039* (2013.01)

(58) Field of Classification Search
USPC ........... 623/1.13, 1.15, 1.3–1.31, 23.64, 23.7
See application file for complete search history.

(56) References Cited

U.S. PATENT DOCUMENTS

| | | |
|---|---|---|
| 5,061,275 A | 10/1991 | Wallsten et al. |
| 5,152,797 A | 10/1992 | Luckman et al. |
| 5,607,445 A | 3/1997 | Summers |
| 5,662,713 A | 9/1997 | Andersen et al. |
| 5,733,327 A | 3/1998 | Igaki et al. |
| 5,766,263 A | 6/1998 | Grundei et al. |
| 5,827,321 A | 10/1998 | Roubin et al. |
| 5,833,707 A | 11/1998 | McIntyre et al. |
| 5,843,175 A | 12/1998 | Frantzen |
| 6,221,091 B1 | 4/2001 | Khosravi |
| 6,254,642 B1 | 7/2001 | Taylor |
| 6,264,700 B1 | 7/2001 | Kilcoyne et al. |
| 6,302,917 B1 | 10/2001 | Dua et al. |
| 6,348,065 B1 * | 2/2002 | Brown ............... A61F 2/91 606/198 |

(Continued)

FOREIGN PATENT DOCUMENTS

| | | |
|---|---|---|
| CN | 1433818 A | 8/2003 |
| CN | 201200504 | 3/2009 |

(Continued)

OTHER PUBLICATIONS

Material Safety Data Sheet, © 2010 Polymer Systems Technology Limited™, UK & Ireland Distributor, NUSIL Silicone Technology. Effective Feb. 8, 2010. pp. 1-9.

(Continued)

*Primary Examiner* — Leslie Lopez
(74) *Attorney, Agent, or Firm* — Stoel Rives LLP (57) ABSTRACT

A stent comprised of a scaffolding structure having components configured to allow at least a portion of the stent to decrease in diameter in response to an axial force applied to the stent. Further, the components and elements of the stent may be configured to balance transverse forces applied to the stent, thus reducing the incidence of infolding.

20 Claims, 9 Drawing Sheets

(56) References Cited

U.S. PATENT DOCUMENTS

| | | | |
|---|---|---|---|
| 6,464,720 B2 | 10/2002 | Boatman et al. | |
| 6,511,505 B2* | 1/2003 | Cox et al. | 623/1.16 |
| 6,544,291 B2 | 4/2003 | Taylor | |
| 6,585,758 B1 | 7/2003 | Chouinard et al. | |
| 6,635,082 B1 | 10/2003 | Hossainy et al. | |
| 6,669,724 B2 | 12/2003 | Park et al. | |
| 6,701,174 B1 | 3/2004 | Krause et al. | |
| 6,845,776 B2 | 1/2005 | Stack et al. | |
| 6,878,162 B2* | 4/2005 | Bales et al. | 623/1.15 |
| 6,913,619 B2 | 7/2005 | Brown et al. | |
| 6,929,658 B1* | 8/2005 | Freidberg et al. | 623/1.13 |
| 6,966,928 B2 | 11/2005 | Fell et al. | |
| 6,991,647 B2 | 1/2006 | Jadhav | |
| 7,462,192 B2 | 12/2008 | Norton et al. | |
| 7,488,347 B1 | 2/2009 | Goble et al. | |
| 7,547,321 B2 | 6/2009 | Silvestri et al. | |
| 7,637,942 B2 | 12/2009 | Mangiardi et al. | |
| 7,641,694 B1 | 1/2010 | Goble et al. | |
| 7,695,446 B2 | 4/2010 | Levine et al. | |
| 7,722,624 B2 | 5/2010 | Boucher et al. | |
| 8,361,147 B2 | 1/2013 | Shterling et al. | |
| 8,500,821 B2 | 8/2013 | Sobrino-Serrano et al. | |
| 8,523,936 B2 | 9/2013 | Schmid et al. | |
| 8,579,985 B2 | 11/2013 | Podolsky et al. | |
| 8,632,600 B2 | 1/2014 | Zannis et al. | |
| 8,986,368 B2 | 3/2015 | Gill et al. | |
| 2002/0032479 A1 | 3/2002 | Hankh et al. | |
| 2002/0068967 A1* | 6/2002 | Drasler et al. | 623/1.13 |
| 2002/0107565 A1 | 8/2002 | Greenhalgh | |
| 2002/0116052 A1* | 8/2002 | Cox et al. | 623/1.16 |
| 2002/0138135 A1 | 9/2002 | Duerig et al. | |
| 2003/0009236 A1 | 1/2003 | Godin | |
| 2003/0060884 A1 | 3/2003 | Fell et al. | |
| 2003/0109878 A1 | 6/2003 | Grundei | |
| 2003/0109879 A1 | 6/2003 | Grundei | |
| 2003/0220700 A1 | 11/2003 | Hammer et al. | |
| 2004/0019374 A1 | 1/2004 | Hojeibane et al. | |
| 2004/0044401 A1* | 3/2004 | Bales | A61F 2/88 623/1.22 |
| 2004/0068324 A1 | 4/2004 | Grundei | |
| 2004/0088040 A1 | 5/2004 | Mangiardi et al. | |
| 2004/0102866 A1 | 5/2004 | Harris et al. | |
| 2004/0107004 A1 | 6/2004 | Levine et al. | |
| 2004/0116996 A1 | 6/2004 | Freitag | |
| 2004/0127973 A1* | 7/2004 | Mangiardi | A61F 2/915 623/1.15 |
| 2004/0204749 A1 | 10/2004 | Gunderson | |
| 2004/0236424 A1 | 11/2004 | Berez et al. | |
| 2004/0267350 A1 | 12/2004 | Roubin et al. | |
| 2005/0033424 A1 | 2/2005 | Fell | |
| 2005/0102038 A1 | 5/2005 | Grundei | |
| 2005/0143745 A1 | 6/2005 | Hadorek et al. | |
| 2005/0169893 A1 | 8/2005 | Koblish et al. | |
| 2005/0183731 A1 | 8/2005 | Hunter et al. | |
| 2006/0157543 A1 | 7/2006 | Abkowitz et al. | |
| 2006/0212052 A1 | 9/2006 | Shin et al. | |
| 2006/0253190 A1 | 11/2006 | Kuo | |
| 2006/0259137 A1 | 11/2006 | Artof et al. | |
| 2006/0276874 A1 | 12/2006 | Wilson et al. | |
| 2007/0038290 A1 | 2/2007 | Huang et al. | |
| 2007/0050011 A1 | 3/2007 | Klein et al. | |
| 2007/0050021 A1 | 3/2007 | Johnson | |
| 2007/0100437 A1* | 5/2007 | Welborn | A61F 2/07 623/1.44 |
| 2007/0112437 A1 | 5/2007 | Shank | |
| 2007/0150049 A1* | 6/2007 | Nissl | 623/1.16 |
| 2007/0173946 A1 | 7/2007 | Bonutti | |
| 2007/0198022 A1 | 8/2007 | Lang et al. | |
| 2007/0198097 A1 | 8/2007 | Zegid | |
| 2007/0239273 A1 | 10/2007 | Allen | |
| 2007/0255412 A1 | 11/2007 | Hajaj et al. | |
| 2007/0276463 A1 | 11/2007 | Nissl et al. | |
| 2008/0004688 A1 | 1/2008 | Spenser et al. | |
| 2008/0097579 A1* | 4/2008 | Shanley et al. | 623/1.16 |
| 2008/0132998 A1 | 6/2008 | Mangiardi et al. | |
| 2008/0133020 A1 | 6/2008 | Blackwell et al. | |
| 2008/0140181 A1 | 6/2008 | Reynolds et al. | |
| 2008/0154351 A1 | 6/2008 | Leewood et al. | |
| 2008/0200979 A1 | 8/2008 | Dieck et al. | |
| 2008/0221664 A1 | 9/2008 | Bales et al. | |
| 2008/0221670 A1 | 9/2008 | Clerc | |
| 2008/0243225 A1* | 10/2008 | Satasiya | A61F 2/91 623/1.12 |
| 2008/0288044 A1* | 11/2008 | Osborne | A61F 2/07 623/1.13 |
| 2009/0036976 A1 | 2/2009 | Beach et al. | |
| 2009/0043373 A1 | 2/2009 | Arnault de la Menardiere et al. | |
| 2009/0105809 A1* | 4/2009 | Lee et al. | 623/1.17 |
| 2009/0118830 A1 | 5/2009 | Fell | |
| 2009/0171456 A1 | 7/2009 | Kveen et al. | |
| 2009/0171465 A1 | 7/2009 | Bucay-Couto et al. | |
| 2009/0187240 A1 | 7/2009 | Clerc | |
| 2009/0240320 A1* | 9/2009 | Tuval | A61F 2/2418 623/1.24 |
| 2010/0004728 A1* | 1/2010 | Rao et al. | 623/1.11 |
| 2010/0036504 A1 | 2/2010 | Sobrino-Serrano et al. | |
| 2010/0082093 A1 | 4/2010 | Weber | |
| 2010/0114327 A1 | 5/2010 | Sobrino-Serrano et al. | |
| 2010/0121461 A1* | 5/2010 | Sobrino-Serrano | A61F 2/04 623/23.68 |
| 2010/0121462 A1 | 5/2010 | Sobrino-Serrano et al. | |
| 2010/0137998 A1 | 6/2010 | Sobrino-Serrano et al. | |
| 2010/0173066 A1 | 7/2010 | Mangiardi et al. | |
| 2010/0256744 A1 | 10/2010 | Laborde et al. | |
| 2010/0286760 A1 | 11/2010 | Beach et al. | |
| 2011/0004290 A1 | 1/2011 | Bales, Jr. et al. | |
| 2011/0054592 A1 | 3/2011 | Fliedner | |
| 2011/0190874 A1 | 8/2011 | Celermajer et al. | |
| 2011/0190905 A1 | 8/2011 | Behan | |
| 2011/0265908 A1 | 11/2011 | Clerc | |
| 2012/0010697 A1 | 1/2012 | Shin et al. | |
| 2012/0059486 A1 | 3/2012 | Sobrino-Serrano et al. | |
| 2012/0071987 A1 | 3/2012 | Levy | |
| 2013/0006382 A1 | 1/2013 | Behan | |
| 2013/0103163 A1 | 4/2013 | Krimsky et al. | |

FOREIGN PATENT DOCUMENTS

| | | |
|---|---|---|
| EP | 1870057 | 12/2007 |
| EP | 2329796 | 6/2011 |
| EP | 2489331 | 8/2012 |
| JP | 2002525162 | 8/2002 |
| JP | 2007507301 | 3/2007 |
| JP | 2010522015 | 7/2010 |
| WO | 198203052 | 2/1982 |
| WO | 200018322 | 4/2000 |
| WO | 2005/089672 A1 | 9/2005 |
| WO | WO2005/089672 | 9/2005 |
| WO | 2006/047520 A2 | 5/2006 |
| WO | WO2006/047520 | 5/2006 |
| WO | 2006/069094 A1 | 6/2006 |
| WO | WO2006/069094 | 6/2006 |
| WO | WO 2010/098857 | 9/2010 |
| WO | WO 2011/104269 | 9/2011 |
| WO | WO2012/103501 | 8/2012 |

OTHER PUBLICATIONS

International Search Report and Written Opinion dated Aug. 16, 2012 for PCT/US12/35851.
International Search Report and Written Opinion dated Mar. 29, 2013 for PCT/US2012/060364.
Restriction Requirement dated May 6, 2014 for U.S. Appl. No. 13/909,427.
International Search Report and Written Opinion dated Jul. 1, 2014 for PCT/US2012/022328.
Office Action dated Jan. 29, 2015 for U.S. Appl. No. 13/352,926.
European Search Report dated Feb. 18, 2015 for EP12793791.0.
Office Action dated Oct. 17, 2014 for U.S. Appl. No. 13/909,427.
Office Action dated Mar. 13, 2015 for U.S. Appl. No. 14/196,012.
Office Action dated Jun. 19, 2014 for U.S. Appl. No. 13/352,926.
Office Action dated Sep. 28, 2015 for U.S. Appl. No. 14/196,012.

(56) References Cited

OTHER PUBLICATIONS

Final Office Action dated Jun. 30, 2015 for U.S. Appl. No. 13/909,427.
International Search Report and Written Opinion dated May 15, 2014 for PCT/US2012/060364.
International Search Report and Written Opinion dated Jun. 10, 2014 for PCT/US2014/020187.
International Search Report and Written Opinion dated Jul. 1, 2014 for PCT/US2014/022328.
International Search Report and Written Opinion dated Sep. 13, 2013 for PCT/US2013/044013.
International Search Report and Written Opinion dated Oct. 16, 2012 for PCT/US2012/060364.
Notice of Allowance dated Dec. 23, 2014 for U.S. Appl. No. 13/285,358.
Office Action dated Jan. 6, 2014 for U.S. Appl. No. 13/285,358.
Office Action dated Apr. 9, 2015 for U.S. Appl. No. 14/202,128.
Office Action dated May 15, 2013 for U.S. Appl. No. 13/285,358.
Office Action dated Feb. 17, 2016 for U.S. Appl. No. 14/196,012.
Office Action dated Mar. 22, 2016 for U.S. Appl. No. 14/661,562.
Office Action dated Mar. 29, 2016 for U.S. Appl. No. 14/202,128.
Office Action dated May 11, 2016 for U.S. Appl. No. 13/909,427.
Notice of Allowance dated Aug. 26, 2016 for U.S. Appl. No. 14/196,012.
Office Action dated Oct. 25, 2016 for U.S. Appl. No. 14/661,562.
Office Action dated Nov. 8, 2016 for U.S. Appl. No. 14/202,128.
Office Action dated Dec. 19, 2016 for U.S. Appl. No. 13/909,427.
Notice of Allowance dated May 18, 2017 for U.S. Appl. No. 14/661,562.
Office Action Aug. 31, 2017 for U.S. Appl. No. 14/202,128.
Notice of Allowance dated May 5, 2017 for U.S. Appl. No. 13/909,427.
Office Action dated Feb. 28, 2017 for U.S. Appl. No. 14/202,128.
Office Action dated Aug. 16, 2018 for U.S. Appl. No. 14/202,128.

\* cited by examiner

ESOPHAGEAL STENT

TECHNICAL FIELD

The present disclosure relates generally to devices configured to be implanted within a body lumen. More particularly, the present disclosure relates to stents or similar prosthetic devices which, in certain embodiments, are configured to be disposed within the esophagus.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 1AA is a further close up view of a portion of FIG. 1.

FIG. 6 is a side view of a stent in an unexpanded state. More particularly.

DETAILED DESCRIPTION

A stent may be configured with a support or scaffolding structure that may optionally be coupled to a covering. Additionally, the stent may comprise a variety of components, the parameters of these components—such as shape, length, thickness, position, etc.—may be configured to provide a stent with certain properties. For example, the stent may be configured to distribute transverse loads or to change shape in response to certain forces. In some embodiments, the stent may also include a suture which may aid the user with repositioning or removal of the stent.

Though many of the examples provided herein refer to stents configured for use within the esophagus, the present disclosure is also applicable to a variety of stents designed for a variety of applications. For example, biliary stents, bronchial stents, tracheal stents, colonic/duodenal stents, and so on.

It will be readily understood that the components of the embodiments, as generally described and illustrated in the figures herein, could be arranged and designed in a variety of configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

The phrases "connected to," "coupled to," and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" refer to opposite ends of a medical device. As used herein, the proximal end of a medical device is the end nearest a practitioner during use, while the distal end is the opposite end. For example, the proximal end of a stent refers to the end nearest the practitioner when the stent is disposed within, or being deployed from, a deployment device. For consistency throughout, these terms remain constant in the case of a deployed stent, regardless of the orientation of the stent within the body. In the case of an esophageal stent—deployed through the mouth of a patient—the proximal end will be nearer the head of the patient and the distal end nearer the stomach when the stent is in a deployed position.

Figure 1:
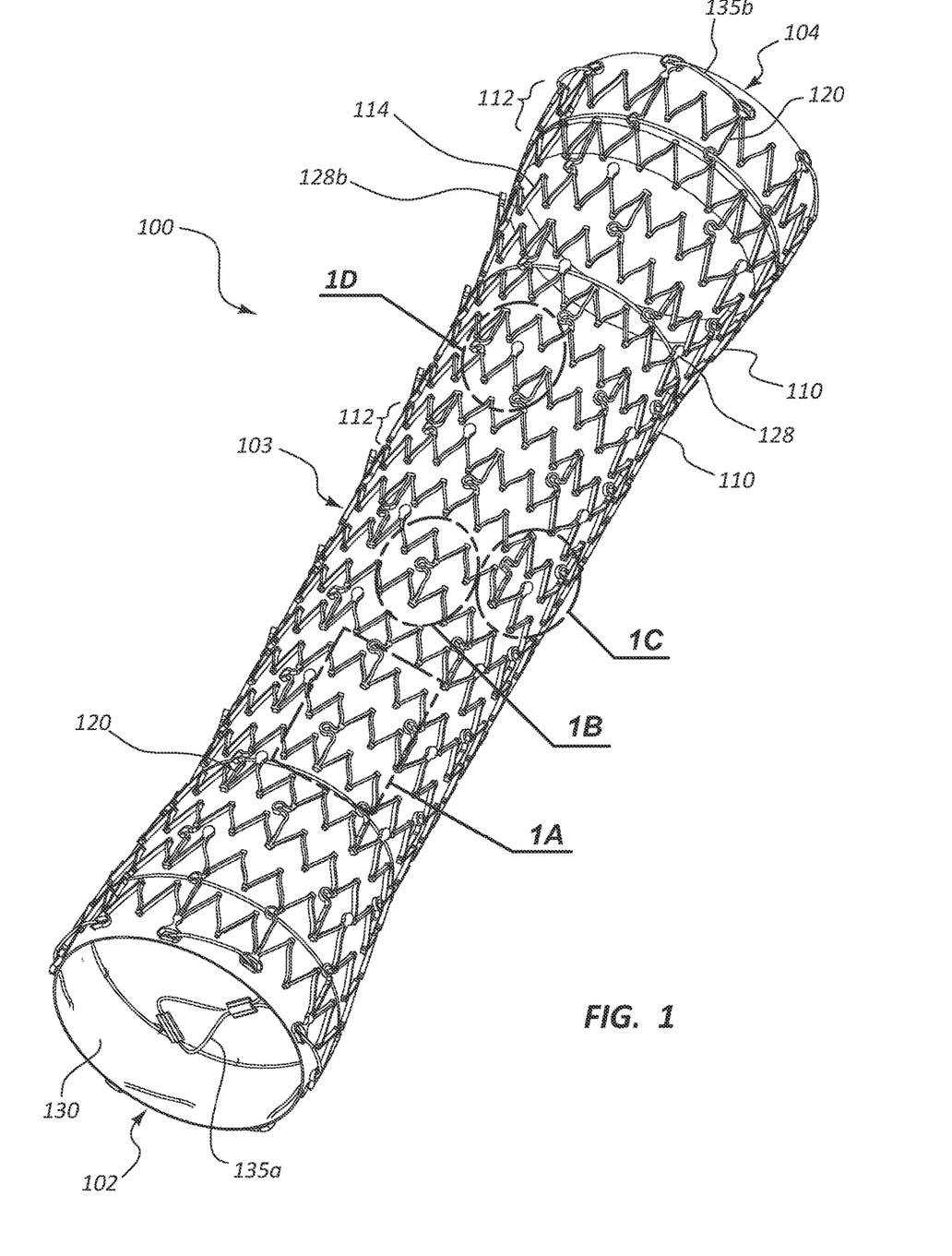
FIG. 1 is a perspective view of a stent.

FIG. 1 is a perspective view of one embodiment of a stent 100. In the illustrated embodiment, the stent 100 has a substantially cylindrical shape and defines a proximal end 102 and a distal end 104. The stent 100 may include a scaffolding structure 110 formed of multiple interconnected segments, a covering 130 coupled to the scaffolding structure 110, and one or more sutures 135a, 135b.

The scaffolding structure 110 may be comprised of any material known in the art, including memory alloys. In some embodiments the scaffolding structure 110 may be constructed of nitinol. The thickness of the scaffolding structure 110 may be from about 0.3 mm to about 0.6 mm, or greater, in some embodiments, including thicknesses from about 0.35 mm to about 0.55 mm, thicknesses from about 0.4 mm to about 0.5 mm, and thicknesses of about 0.47 mm.

The scaffolding structure 110 may be formed of multiple annular segments or rings 112 arranged in rows along the longitudinal direction of the stent 100. Each annular segment 112 may be comprised of interconnected strut arms 114. In the illustrated embodiment, the strut arms 114 are connected such that they form a zigzag pattern, the pattern defining alternating "peaks" and "valleys," around the annular segment 112. In some embodiments adjacent strut arms 114 will form acute angles relative to each other. Adjacent annular segments 112 may be coupled to each other by connectors 120.

Figures 1, 1A, 1B, 1C, 1D:
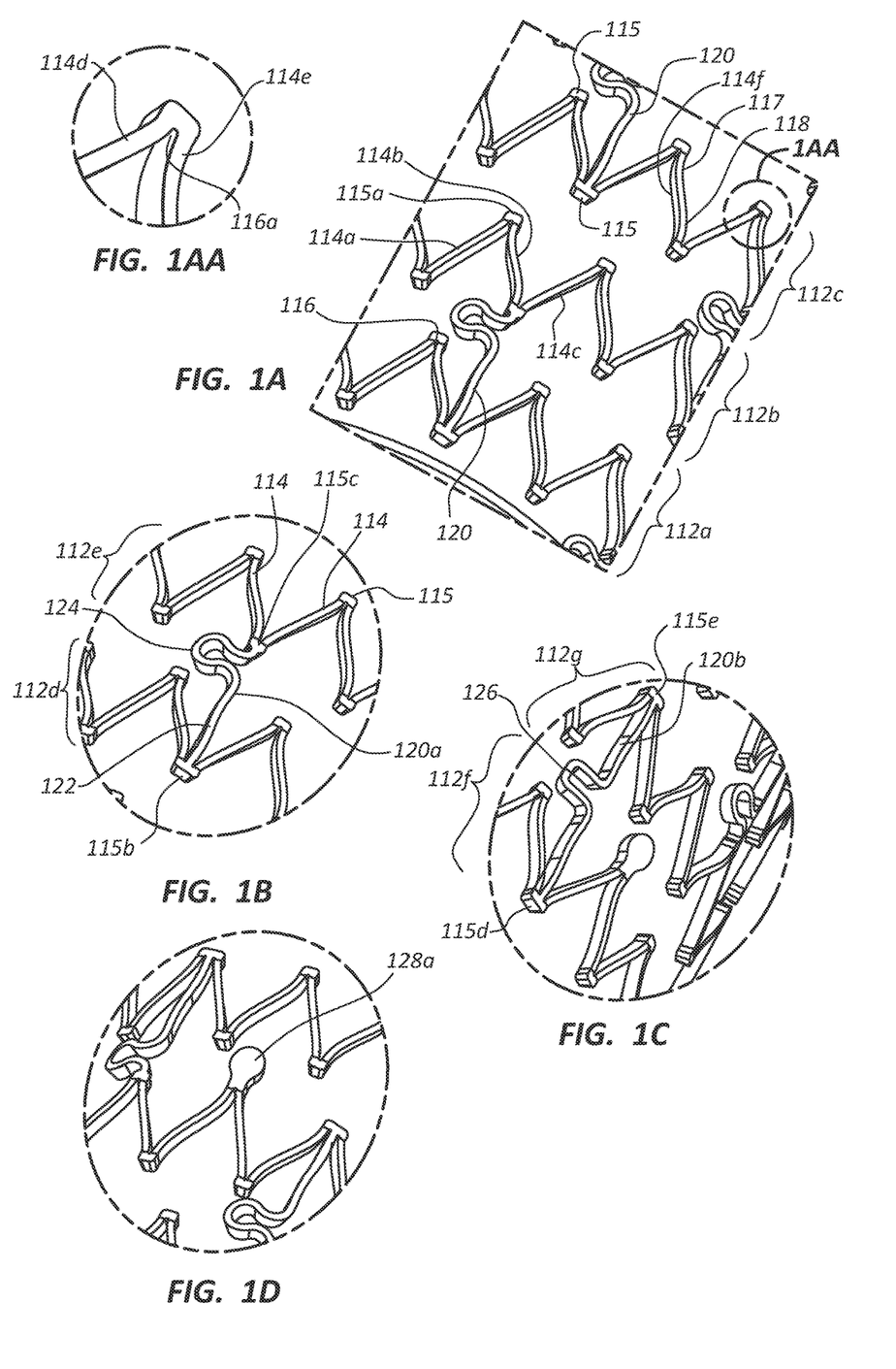
FIG. 1A is a close up view of a portion of the stent of FIG. 1.
FIG. 1B is a second close up view of a portion of the stent of FIG. 1.
FIG. 1C is a third close up view of a portion of the stent of FIG. 1.
FIG. 1D is a fourth close up view of a portion of the stent of FIG. 1.

FIG. 1A is a close up view of a portion of the stent 100 of FIG. 1. FIG. 1A includes portions of three adjacent annular segments, designated 112a, 112b, and 112c. Throughout this disclosure, particular examples of components may be designated by a letter following the reference numeral. For example, reference numeral 112 refers generally to the annular segments of the stent 100. Specific annular segments, such as those shown in FIG. 1A, are thus labeled 112a, 112b, and 112c. This pattern of indentifying particular examples of general or repeating components may be used throughout this disclosure.

In the illustrated embodiment, each annular segment 112a, 112b, 112c includes multiple strut arms 114, which are arranged in zigzag patterns. For example, strut arm 114a is coupled to strut arm 114b, such that the two arms 114a, 114b form a peak in the zigzag pattern. Strut arm 114b is further coupled to strut arm 114c such that the two arms 114b, 114c form a valley in the zigzag pattern.

In the illustrated embodiment, adjacent strut arms, such as arms 114a, 114b, are coupled at an apex, such as apex 115a. The angle formed at the apexes 115 by two adjacent strut arms 114 may be designed to provide the stent 100 with particular properties. For example, in the illustrated embodiment the angle formed at each apex 115 is about 45 degrees. In other embodiments this angle may be from about 30 degrees to about 60 degrees including angles from about 40 degrees to 50 degrees. As discussed in more detail below, apex 115 angles of about 45 degrees, as well as angles within the aforementioned ranges, may aid with balancing forces in the X and Y directions on the stent 100 to prevent infolding of the stent.

In some embodiments, the inner surface of the apex 115 may be substantially circular or semi-circular in shape, forming an inner radius 116. The inner radius 116 of the apex 115 may be sized so as to impart particular characteristics to the stent 100. For example, as illustrated in FIG. 1AA, the radius 116a may be large as compared to the angle formed by the two inner surfaces of the coupled strut arms 114d, 114e. In such instances, the inner surfaces of the strut arms 114 and the radius 116 may form a rough "keyhole" shape. In other embodiments, the radius 116 and strut arms 114 may not form a keyhole shape, though the radius 116 is still relatively large. Designs that incorporate relatively large radii 116 may provide desired characteristics to the stent 100, such as surface finish, fatigue life, and fracture resistance. The size of the radius 116 may vary depending on the desired properties of the stent 100. In some embodiments the radius 116 may be from about 15 microns to about 95 microns including embodiments where the radius is from about 30 microns to about 80 microns or from about 45 microns to about 65 microns.

Each strut arm 114 may define a length along the strut arm 114. Again, as shown in both FIG. 1 and FIG. 1A, each strut arm 114 is coupled to two other strut arms 114, forming apexes 115 on both ends of the strut arm 114. The length of a single strut arm 114 is the length of the strut arm 114 from a first end to a second end, or the distance between each apex 115 at which the strut arm 114 is coupled to an adjacent strut arm 114.

The relative lengths of the strut arms 114 may affect the overall properties of the stent 100. For instance, portions of the stent 100 that have relatively longer strut arms 114 may be "softer" (meaning more compressible in a transverse direction) than portions of the stent 100 where the strut arms 114 are relatively shorter. In the embodiment illustrated in FIG. 1, the stent arms 114 located toward the proximal 102 and distal 104 ends are relatively longer than those located near the mid-body portion 103 of the stent 100. Thus, the stent 100 illustrated in FIG. 1 will generally be stiffer, or less compressible in a transverse direction, in the mid-body section 103 and softer near the proximal 102 and distal 104 ends. The stent 100 of FIG. 1 is designed with substantially the same dimensions and geometry at both the proximal 102 and distal 104 ends. In other embodiments, the stent 100 may also be configured such that the strut arms 114 located near the proximal 102 end are relatively longer than the strut arms 114 located near the distal 104 end. Accordingly, the stent 100 may also be softer near the proximal end 102 relative to the distal end 104. In other embodiments, a stent may be designed with strut arms of uniform length throughout, of a particular length in certain zones (for example, near both the proximal and distal ends), or of varying lengths along the entire stent. Further, in some embodiments, strut arm 114 length will be substantially constant for all strut arms 114 located on the same annular portion 112; in other embodiments strut arm 114 length may vary within a single annular portion 112.

In some embodiments, a stent may be configured with softer zones in order to tailor the stent to a specific therapy. For example, a stent designed with relatively soft ends may result in relatively less discomfort, or pain, caused by contact of the stent ends with body tissue. Thus, in embodiments where the treatment location is near the mid-body of the stent, the stent may be designed such that the mid-body region is relatively stiff—allowing it to resist stricture and otherwise function as part of the treatment—and the ends are relatively soft to reduce trauma and pain at those points. In other embodiments, different zones may be relatively softer, depending on the desired application and therapy.

In certain embodiments, the strut arms 114 may be curved. Strut arm 114f illustrated in FIG. 1A, for example, may be understood as having a first portion 117 and a second portion 118. The first 117 and second 118 portions may or may not be the same length. Strut arm 114f is generally formed with an inflection point located between the first 117 and second 118 portions of the strut arm 114f. Thus, in the illustrated embodiment, the strut arm 114f may be curved in the general shape of a sigmoid curve. In other words, the first portion 117 of the strut arm 114f forms a first roughly arcuate path, and the second portion 118 of the strut arm 114f forms a second roughly arcuate path. In the illustrated embodiment, the center of the first arcuate path is on the opposite side of the arm than the center of the second arcuate path. Thus, the strut arm 114f has a wave-like shape formed by the strut arm 114f starting to curve in one direction, then curving in a second direction. Accordingly, strut arm 114f has an "inflection point" at or around the point where the first portion 117 meets the second portion 118. In the embodiment of FIG. 1, each strut arm 114 is shaped substantially as described in connection with strut arm 114f.

In other embodiments, the strut arms 114 may have a single curve, may be substantially straight, or may resemble other types of curves. Furthermore, while in some instances each strut arm 114 may have a curved shape similar to the other strut arms 114 of the stent 100, in other embodiments multiple strut arms 114 on the same stent—including strut arms 114 disposed in the same annular segment 112—may have different shapes.

As shown in FIGS. 1 and 1A, adjacent annular segments 112 may be coupled by connectors 120. In some embodiments, the connectors 120 may be coupled to the annular segments 112 at the apexes 115 formed by adjacent strut arms 114. In the embodiment of FIGS. 1 and 1A, the connectors 120 are offset in the circumferential direction along the longitudinal direction of the stent 100. Thus, in the illustrated embodiment, any apex 115 is coupled to no more than one connector 120. In other embodiments the connectors 120 may be aligned circumferentially along the longitudinal direction of the stent 100, or aligned in some areas and offset in others.

FIG. 1B is a close up view of a portion of the stent 100 of FIG. 1, showing a single connector 120a. The connector 120a couples two adjacent annular portions 112d, 112e together, and is coupled to each annular portion 112d, 112e at apexes 115b, 115c on each annular portion. Connector 120a has a first portion 122 and a second portion 124. In the illustrated embodiment, the first portion 122 is relatively straight and spans much of the distance between the adjacent annular segments 112. In other embodiments, the first portion 122 may be more or less curved than the first portion 122 of the illustrated embodiment. The second portion 124 may be substantially formed in a rounded shape, in some instances forming the general profile of the symbol "omega." In some embodiments, the omega-shaped second portion 124 may add axial strength to the stent 100. In some instances, axial strength may be desirable for repositioning or removing a stent 100.

Further, in some embodiments, omega shaped connectors may add flexibility and/or elasticity to the stent 100. The omega shape, having two ends relatively near each other connected by a relatively long curved member (the round portion of the omega) may be configured to provide added flexibility to the stent.

The other connectors 120 of the embodiment of FIG. 1 are generally shaped like connector 120a disclosed above, with the exception of the connectors located at the mid-body of the stent 100. It is within the scope of this disclosure, however, to use any type or shape of connector at any point along the stent.

At the portion of the stent 100 shown in FIG. 1B, the adjacent annular segments 112d, 112e are aligned such that apexes 115 at the peak of the zigzag pattern in annular segment 112d are circumferentially aligned with apexes 115 at the peak of the zigzag pattern of the adjacent annular segment 112e. The connector 120a couples the two adjacent annular segments 112d, 112e by coupling to valley apex 115b of annular segment 112d and to valley apex 115c of annular segment 112e. (As used herein, "peaks" refer to high points and "valleys" refer to low points, as measured from one end of the stent. Thus the coupling of the two segments just described may also be described as a "peak" to "peak" connection, if viewed from the opposite orientation.) In some embodiments, a stent may be designed such that the peaks and valleys of adjacent annular segments are circumferentially aligned, such as annular segments 112d and 112e. In other embodiments, the peaks and valleys of adjacent annular segments may be circumferentially offset.

In the embodiment of FIG. 1, the peaks of each annular segment 112 are circumferentially aligned with the peaks of adjacent annular segments 112, at all points along the stent 100 except one set of adjacent annular segments located at the mid-body 103 of the stent 100. In the embodiment of FIG. 1, the proximal end 102 and distal end 104 substantially "mirror" each other about the mid-body 103. FIG. 1C is a detailed view of two adjacent annular segments 112f, 112g located near the mid-body 103 of the stent 100. (Note: Annular segment 112f of FIG. 1C is the same annular segment as annular segment 112e of FIG. 1B.)

Annular segments 112f, 112g are oriented such that the peaks of annular segment 112f are circumferentially aligned with the valleys of annular segment 112g, and the valleys of annular segment 112f are circumferentially aligned with the peaks of annular segment 112g. It will be appreciated by one of skill in the art having the benefit of this disclosure, that in alternative embodiments any combination of alignment/non-alignment of peaks and valleys between any set of annular segments is within the scope of this disclosure.

Annular segments 112f and 112g are coupled to a connector 120b at apex 115d and apex 115e, respectively. Connector 120b extends between each apex 115d, 115e and includes a generally square portion 126 located near the center of the connector 120b. Connectors such as connector 120b, which span between a peak and valley may be configured to impart more flexibility to the stent 100 than relatively shorter peak to valley connectors. As with the omega-shaped connectors disclosed above, it is within the scope of this disclosure to use a connector with a square portion, such as connector 120a, of FIG. 1B, at any point along the stent.

The stent 100 of FIG. 1 further includes generally rounded anti-migration portions 128 coupled to certain apexes 115. FIG. 1D is a close up view of one anti-migration portion 128a. In some embodiments, the anti-migration portion 128a may be configured to contact portions of the inside diameter of a body lumen, and thus restrict migration of the stent 100 within the body lumen. In certain embodiments, the anti-migration portions 128 may be positioned outward of the outside diameter of the stent 100. For example, anti-migration portion 128b of FIG. 1 is disposed outward from the outside diameter of the stent 100. This arrangement allows anti-migration portion 128b to engage the body lumen and minimize migration of the stent 100. In the embodiment of FIG. 1, each anti-migration portion 128 is disposed outwardly as anti-migration portion 128b, though in other embodiments not every anti-migration portion may be so disposed.

In the embodiment of FIG. 1, each anti-migration portion 128 is disposed in a distally oriented direction, thus configured to minimize migration of the stent 100 in the distal direction. In the case of an esophageal stent, such a design may be configured to counteract the peristaltic forces of the esophagus. In other embodiments, some or all of the anti-migration portions 128 may likewise be disposed in the proximally oriented direction.

The stent 100 of FIG. 1 further includes a covering 130 coupled to the scaffolding structure 110, the covering 130 defining an inner portion of the stent 100. The covering 130 may be elastomeric, polymeric, or comprised of any other material known in the art. In some embodiments, the cover may include silicone, while in certain embodiments the cover may be comprised only of silicone.

In some embodiments the cover 130 may include multiple subparts or layers. In some embodiments the cover 130 may be a two part design. Such two part covers may be composed of a base cover which encapsulates the scaffolding structure 110 and a second cover which may be applied after the first cover cures. In certain embodiments the second cover may only be applied to the outside diameter of the stent 100 and may chemically bond to the first cover layer. In some embodiments, one or both of these cover layers may be comprised of particularly low friction silicone, such as Nusil MED-6670. In embodiments which utilize a particularly low friction cover on the outside diameter of the stent 100, the outer cover may be configured to more easily allow the stent to be loaded into a catheter and/or to decrease the catheter size necessary to sheath the stent 100. Further, a low friction coating may be configured to increase the ergonomics of the system, allowing the stent 100 to be more easily deployed from a catheter.

Additionally, the stent 100 of FIG. 1 includes a first suture 135a disposed adjacent the proximal end 102 of the stent 100 and a second suture 135b disposed adjacent the distal end 104 of the stent 100. In some embodiments a stent 100 may also be designed with only a single suture, or no suture at all. One or both sutures 135a, 135b may be configured as repositioning or removal aids, allowing a practitioner to capture a deployed stent.

The features and elements of the stent 100 of FIG. 1 may be configured to create a stent with particular characteristics and features. In addition to the disclosure recited above, the disclosure provided hereinafter—in connection with any figure or discussion—is equally relevant to controlling the characteristics of a finished stent. Any part of the present disclosure may be combined with any other part of the disclosure to configure a stent. Thus, while certain aspects or parameters—for example, strut arm length or flared ends—may be discussed in connection with one embodiment, such disclosure is relevant to all embodiments.

A stent with substantially the geometry and features described in connection with the stent 100 of FIG. 1 may be configured to "neck down" in response to an axial force. In other words, the diameter of the cylindrical stent may be reduced by applying an axial force to the stent. Such necking down may be used in connection with removing or repositioning a deployed stent; the decrease in diameter may pull the stent out of contact with the body lumen, allowing a practitioner to displace the stent while avoiding some trauma to the body lumen.

In some instances this necking down may occur near the ends of the stent, including instances where the stent only necks down at one end of the stent. For example, a practitioner may reposition or remove a stent by first engaging a suture located near one end of the stent. At the suture location the stent may decrease in diameter as force is applied to the suture; in other words the stent may contract or "purse string" as the suture is tightened. In some embodiments the force associated with this "purse string" effect may be understood as a compressive force acting around the circumference of the stent at the suture location.

Additionally, portions of the stent near the suture may neck down as an axial force is applied to the stent, in some instances the stent necking down to a diameter which is less than the mid-body of the stent. In some embodiments, a stent may be configured such that a force of about 2 pounds causes the stent to neck down as described.

In certain embodiments a stent may be configured to decrease in size, due to one or both of the purse string effect and necking down, primarily at the ends of the stent. In some instances, tissue granulation or other tissue ingrowth into the stent may occur primarily at the ends of the stent. Thus, some stents may be configured to decrease in diameter at the ends to allow a practitioner to dislodge the stent ends from the wall of the body lumen, including in cases where there is tissue granulation at the ends of the stent.

As stated above, each of the elements described above may be manipulated to control the necking down characteristics of a stent. In particular, a stent such as stent 100 of FIG. 1 may neck down due to the elasticity of the covering 130, the alternating arrangement of the connectors 120, and the thickness of the scaffolding structure 110. Additionally, the configuration of the geometry at the ends 102, 104 of the stent 100, including suture eyelets (discussed further below), may influence the necking down characteristics of the stent 100. A stent such as stent 100 may neck down as much as 50% in response to an axial force.

A practitioner may begin the process of repositioning or removing a stent, such as stent 100, by first engaging one of the sutures. The sutures may be used to compress one end such that the end is pulled away from the lumen wall. The practitioner may then apply an axial force to the end of the stent, causing a portion of the stent to neck down and pull away from the lumen wall. The practitioner may then reposition or remove the stent with minimal trauma to the body lumen.

Additionally, a stent with design parameters similar to those of stent 100 may be configured to resist "infolding." Infolding refers to inward protrusions or wrinkles that may form along the inside diameter of a stent in response to unbalanced transverse compressive forces on the stent. For example, an esophageal stent may infold as a result of the peristaltic motion of the esophagus. In other instances, a stent may infold due to forces exerted by an uneven portion of the body lumen, such as a stricture or buildup of scar tissue.

A cylindrical stent may define a set of transverse planes located perpendicular to the longitudinal axis of the stent. As used herein, transverse forces are forces acting in any of these planes. Further, as used herein, the X and Y directions refer to a coordinate system in any of these planes. A stent designed to generally balance compressive forces in the X and Y directions may tend to resist infolding. In other words, a stent may have compressive forces applied unevenly in different transverse directions. The design of the stent may be configured to transfer these forces such that the stent distributes the load more evenly around the circumference of the stent.

In particular, the alternating alignment of the connectors as well as the thickness of the scaffolding structure may be configured to enable a stent, such as stent 100, to resist infolding. For example, in some instances the alternating alignment of the connectors may tend to localize stent deformation caused by strictures in the lumen, rather than transferring such deformations along the length of the stent. Further, the approximately 45 degree angles between adjacent arm struts 114 in stent 100 may transfer uneven loads further allowing the stent 100 to resist infolding. Likewise, other angles disclosed herein may also distribute transverse forces.

Figure 2:
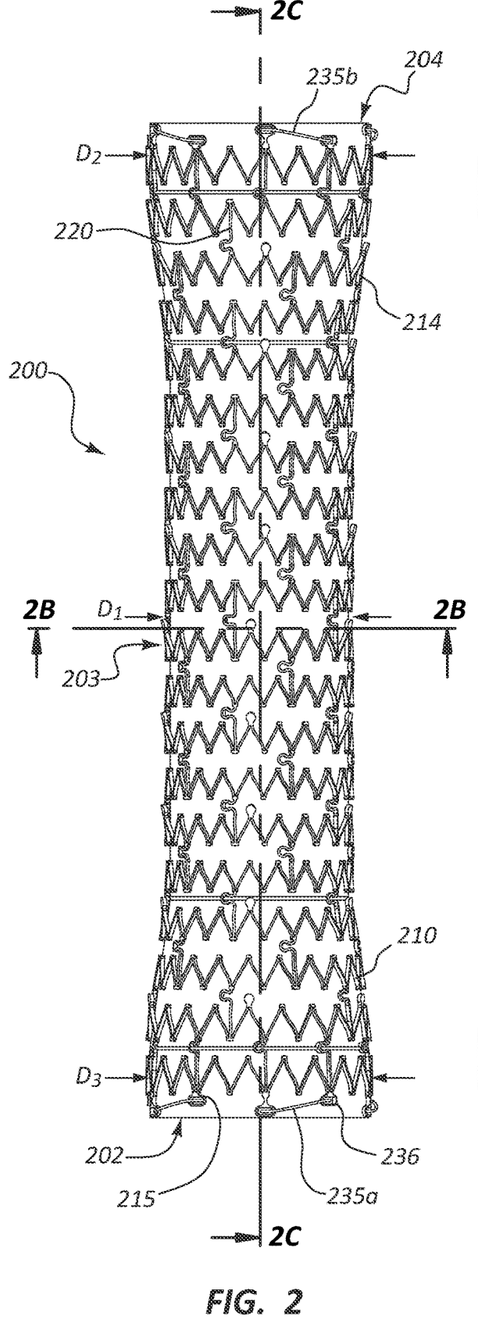
FIG. 2 is a front view of another embodiment of a stent.

FIG. 2 is a front view of another embodiment of a stent that can, in certain respects, resemble components of the stent described in connection with FIGS. 1 and 1A-1D above. It will be appreciated that all the illustrated embodiments may have analogous features. Accordingly, like features are designated with like reference numerals, with the leading digits incremented to "2." (For instance, the stent is designated "100" in FIG. 1 and an analogous stent is designated as "200" in FIG. 2.) Relevant disclosure set forth above regarding similarly identified features thus may not be repeated hereafter. Moreover, specific features of the stent and related components shown in FIG. 2 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the stent of FIG. 2. Any suitable combination of the features, and variations of the same, described with respect to the stent and components illustrated in FIGS. 1 and 1A-1D, can be employed with the stent and components of FIG. 2, and vice versa. This pattern of disclosure applies equally to further embodiments depicted in subsequent figures and described hereafter.

FIG. 2 is a front view of another embodiment of a stent 200. The stent 200 defines a proximal end 202 and a distal end 204 as well as a mid-body section 203. In some embodiments the stent 200 may have a smaller diameter near the mid-body section 203 than sections of the stent 200 near the proximal 202 and distal ends 204. Thus, in the illustrated embodiment, $D_2$ and $D_3$ may be larger in magnitude than $D_1$. In some embodiments, the mid-body diameter may be constant along a length of the stent 200, with transition portions that gradually increase in diameter near the ends 202, 204. Depending on the desired application, the diameters of the stent 200 may vary. For example, certain stents may be designed with mid-body diameters of about 12 mm to about 25 mm, including stents with diameters from about 19 mm to about 23 mm. In embodiments which include flared zones near the ends of the stent, the diameter of the flared sections may increase to about 2 mm greater to about 8 mm greater than the mid-body diameter of the stent, including increases of about 4 mm to about 6 mm or an increase of about 5 mm.

In embodiments where the strut arms 214 are relatively longer (creating relatively "softer" zones near the ends 202, 204 of the stent 200) the transition or flare section may correlate with the zones of the stent 200 that have relatively longer strut arms 214. The strut arm 214 length may be configured to gradually increase along the longitudinal direction of the stent 200 in the flare zones.

Similarly, the length of the connectors 220 may gradually increase as the strut arm 214 length increases. Longer connectors 220 and arm struts 214 may generally create a more open scaffolding structure 210 near the ends 202, 204 of the stent 200. In some embodiments, the flare zones may be mirror images of each other, in other embodiments they may be different.

In some embodiments, the flare zones may be formed by stretching or expanding the ends 202, 204 of the stent 200 with respect to the mid-body 203 of the stent 200. This may result in a more open scaffolding structure 210 near the ends of the stent 200. Regions of the stent 200 with a more open scaffolding structure 210 may be relatively softer than regions of the stent 200 which have a denser scaffolding structure 210. Thus, the flared ends of a stent, such as stent 200, may be configured to create a stent with ends which are softer than the mid-body 203 of the stent. As disclosed above, relatively longer strut arms 214 and connectors 220 may also be configured to create softer regions on a stent. Flared ends and changing strut arm 214 and connector 220 lengths may each be designed and/or may utilize independently from, or in connection with, these other parameters in order to create a stent 200 with relatively softer, or stiffer, zones.

The stent 200 may be configured to neck down in a similar manner to that described in connection with the stent 100 of FIG. 1. In some embodiments, the flared portions of the stent 200 may be configured to neck down to a diameter less than the diameter of a mid-body section of the stent. In certain embodiments, a mid-body section may not be configured to neck down.

Figure 2A:
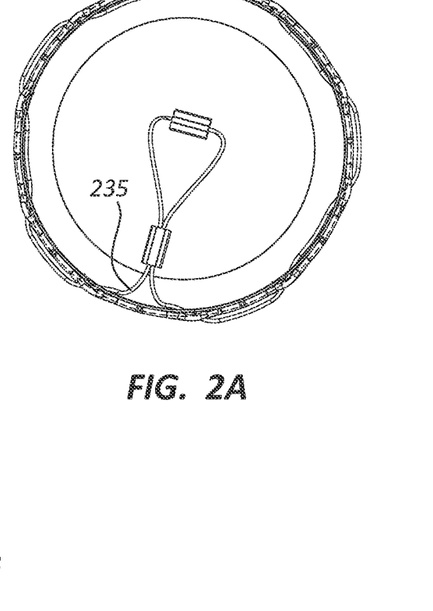
FIG. 2A is a top view of the stent of FIG. 2.
Figure 2B:
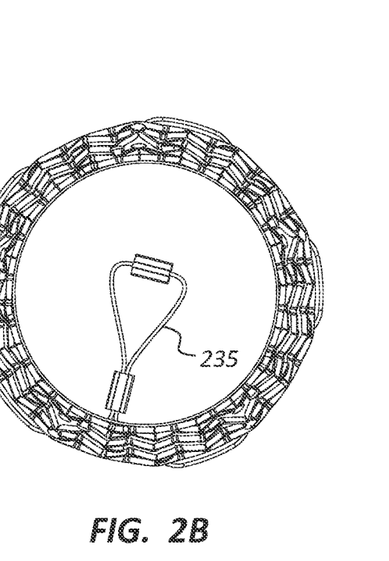
FIG. 2B is a cross-sectional view of the stent of FIG. 2, taken through line 2B-2B.
Figure 2C:
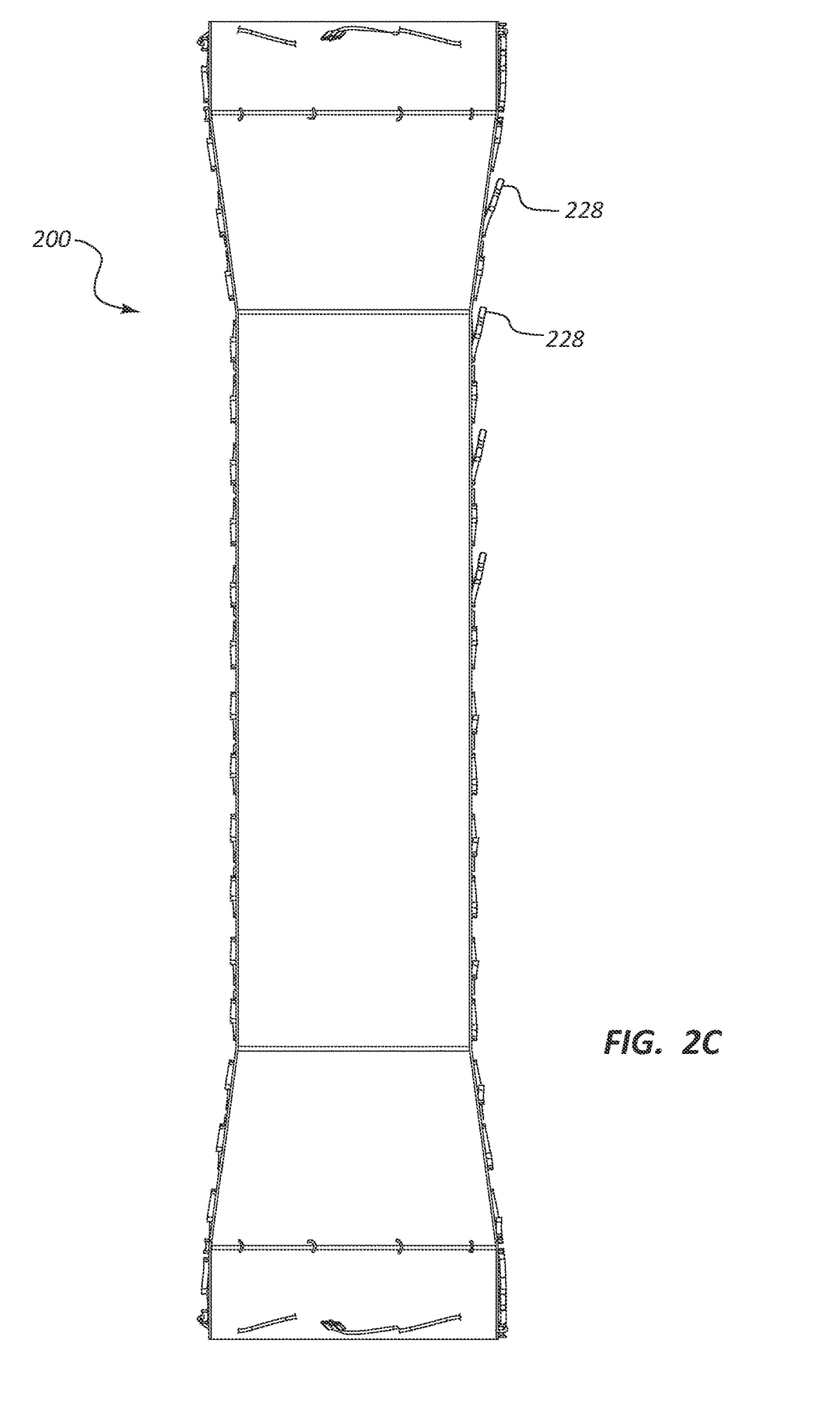
FIG. 2C is a second cross-sectional view of the stent of FIG. 2, taken through line 2C-2C.

FIGS. 2A-2C are additional views of the stent 200 of FIG. 2. FIG. 2A is a top view of the stent of FIG. 2; FIG. 2B is a cross-sectional view of the stent of FIG. 2, taken through line 2B-2B; and FIG. 2C is a second cross-sectional view of the stent of FIG. 2, taken through line 2C-2C. As shown in FIGS. 2, 2A, and 2B, the stent 200 may include suture threading eyelets 236 or apertures, coupled to one or more apexes 215 of the scaffolding structure 210 at the proximal 202 and distal 204 ends of the stent 200. The suture threading eyelets 236 may be configured to receive a suture 235a, 235b and couple it to the stent 200.

Furthermore, the suture threading eyelets 236 may comprise holes or apertures which are elongated in the circumferential direction of the stent 200. Such a design may be configured to distribute the expansive force of a stent 200 acting on a body lumen when the stent 200 is deployed. This distribution of force, in connection with the smooth and rounded shape of the eyelets 236, may be configured to lessen the trauma to body tissue which contacts the ends 202, 204 of the stent 200.

The suture threading eyelets 236 may be configured to locate the sutures 235a, 235b substantially at the proximal 202 or distal 204 ends of the stent 200. Such positioning may be configured to create a relatively uniform purse string effect when the suture 235a, 235b is engaged. In some embodiments, the uniformity of the purse string effect may be influenced by the proximity of the suture threading eyelets 236 to the ends 202, 204 of the stent 200. In other embodiments, the uniformity of the purse string effect may, instead or also, be due to the elongated nature of the eyelets 236 which may allow a suture 235a, 235b to more readily slide through the eyelets 236 during tightening.

FIG. 2C additionally illustrates how the anti-migration portions 228 may be disposed outwardly from the outer diameter of the stent 200, as also disclosed above.

Figures 3A, 3B, 3C:
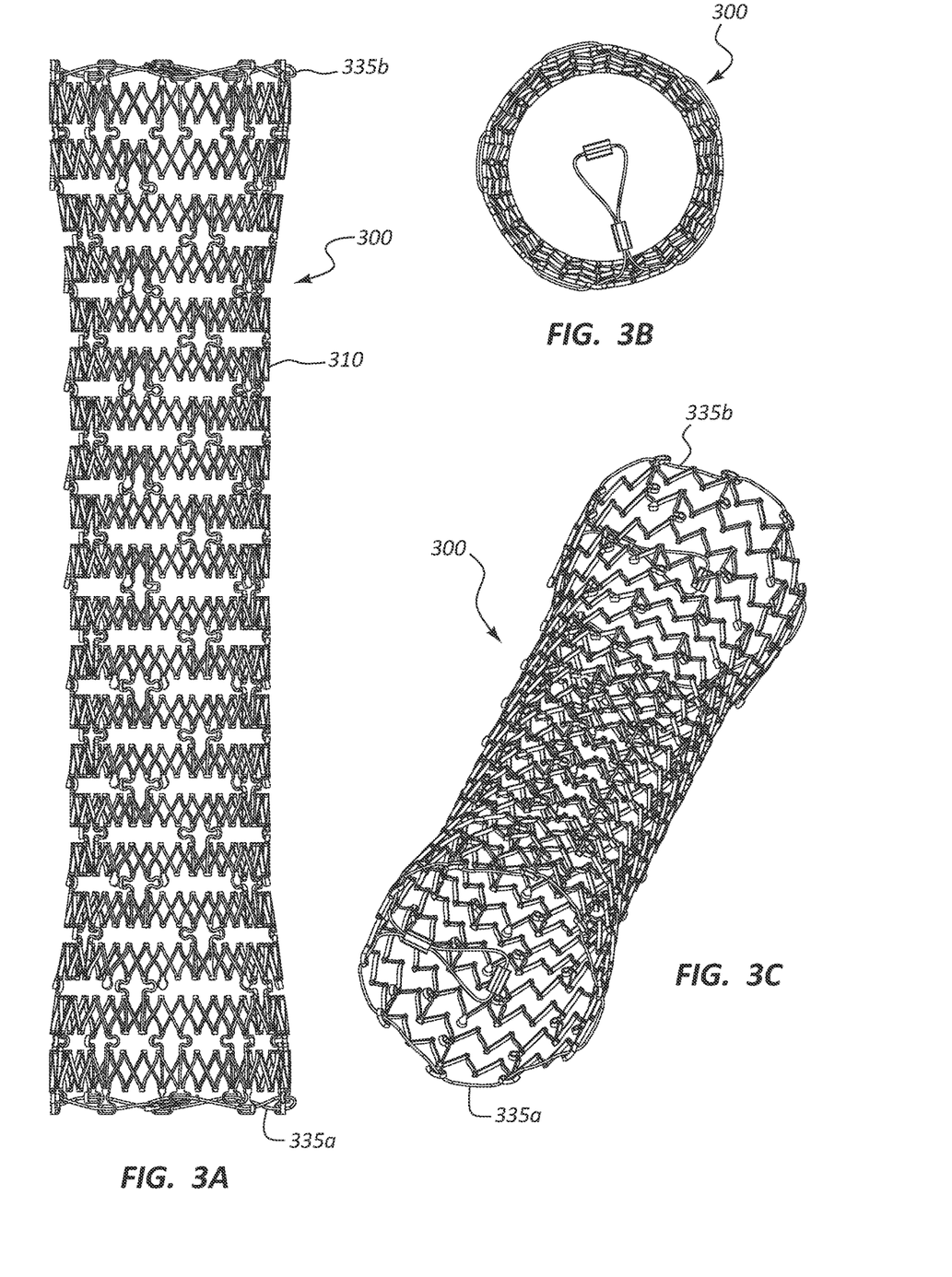
FIG. 3A is a front view of another embodiment of a stent.
FIG. 3B is a top view of the stent of FIG. 3A.
FIG. 3C is a perspective view of the stent of FIG. 3A.
Figure 4A:
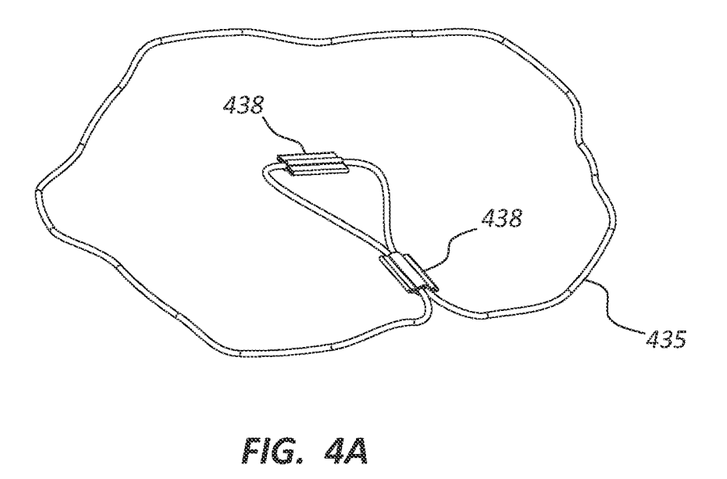
FIG. 4A is a perspective view of a suture for use with a stent.
Figure 4B:
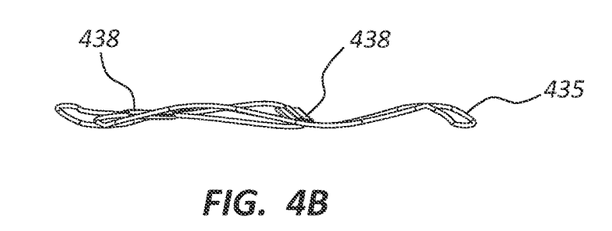
FIG. 4B is a front view of the suture of FIG. 4A.
Figure 4C:
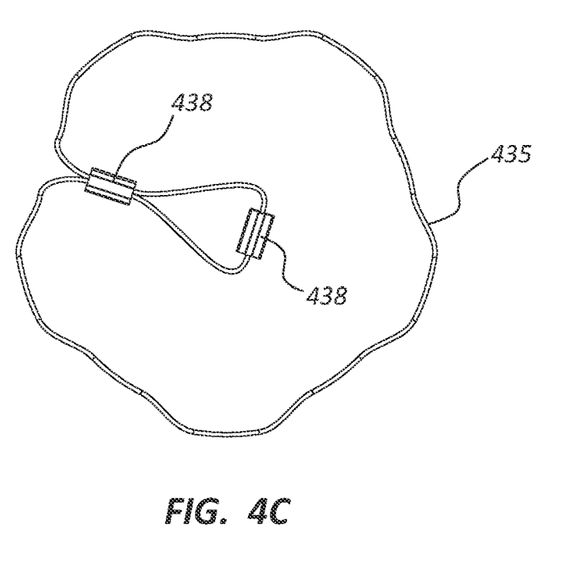
FIG. 4C is a side view of the suture of FIG. 4A.
Figure 4D:
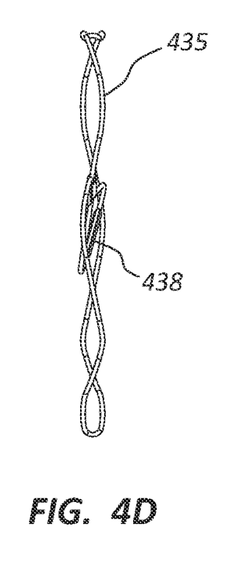
FIG. 4D is a top view of the suture of FIG. 4A.

FIGS. 3A-3C illustrate another embodiment of a stent 300: FIG. 3A is a front view of this embodiment of stent 300; FIG. 3B is a top view of the stent 300 of FIG. 3A; and FIG. 3C is a perspective view of the stent 300 of FIG. 3A. In the embodiment of FIGS. 3A-3C, the stent 300 includes a scaffolding structure 310 and sutures 335a, 335b, but no covering.

FIGS. 4A-4D are multiple views of a suture 435 for use in connection with any of the stents herein disclosed. The suture 435 may be configured to allow a practitioner to engage the suture 435 in order to aid in removing and/or repositioning the stent. In some instances this may be accomplished by the practitioner grasping and displacing the suture 435 through use of a remote access tool, such as grasping forceps. The suture 435 may be formed of a metal, a thread, or any other material. In some embodiments, the suture 435 may comprise one or more radio-opaque portions 438 for use in deploying, removing, or repositioning a stent. The radio-opaque portions may be formed of a metal, such as gold, and enable a practitioner to distinguish these portions by x-ray or similar methods, thus allowing the practitioner to more easily capture suture 435 of a deployed stent with a remote capturing tool. Similarly, the suture 435 may also or alternatively comprise endoscopic markers, or markers visible through an endoscope, to aid a practitioner in viewing or manipulating the stent in connection with an endoscope. In some embodiments certain markers, such as markers comprised of gold, may be both radio-opaque and visible through an endoscope.

Figure 5:
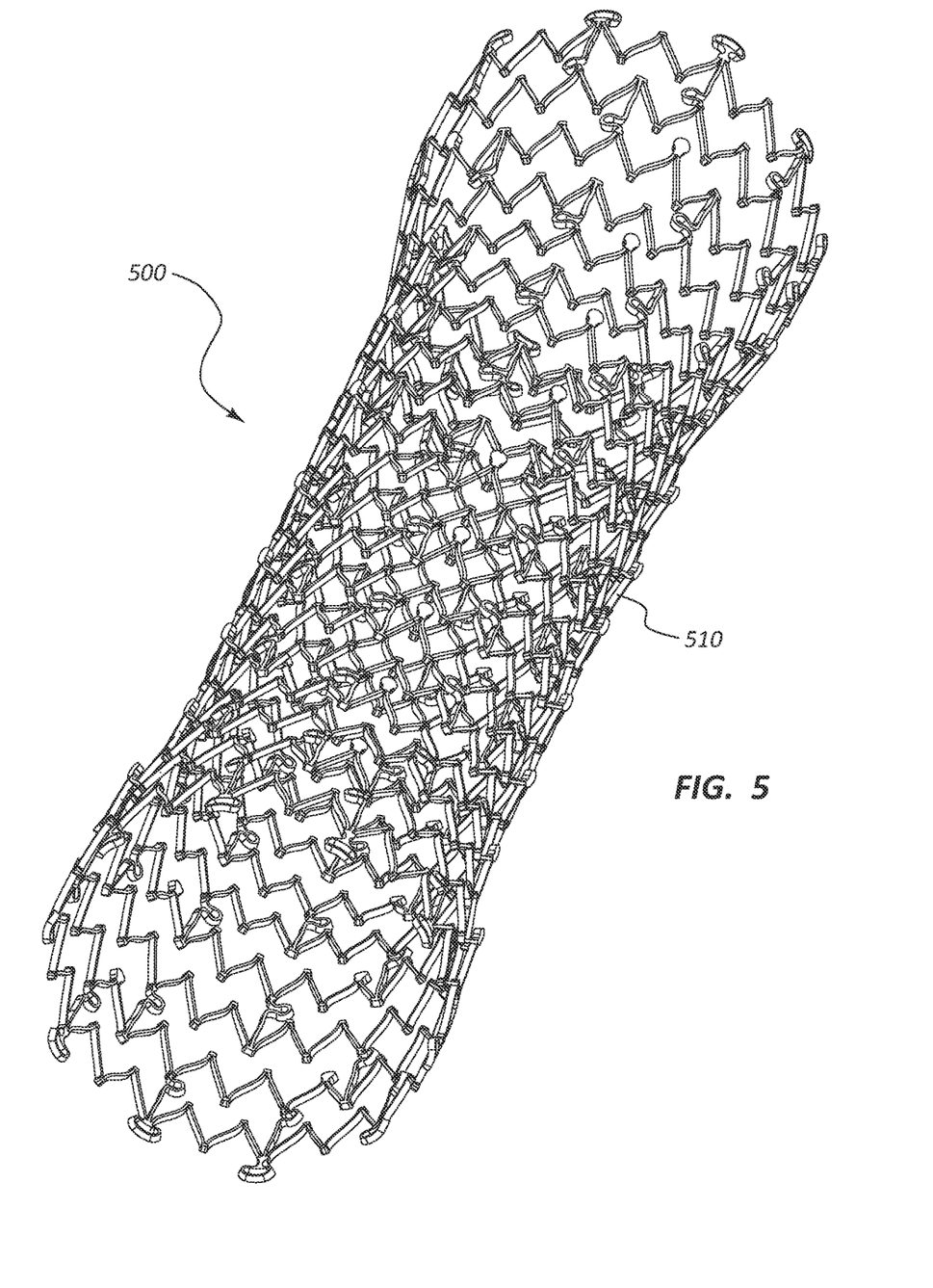
FIG. 5 is a perspective view of another embodiment of a stent.

FIG. 5 is a perspective view of another embodiment of a stent 500, including a scaffolding structure 510. The embodiment of FIG. 5 includes no sutures and no cover.

Figure 6:
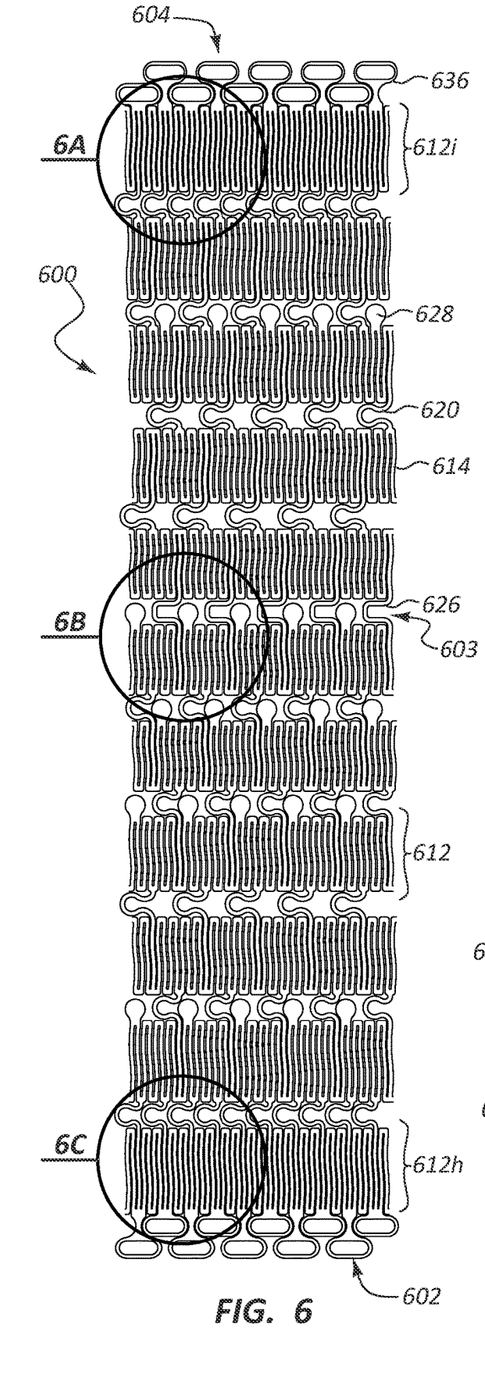
FIG. 6 is a side view of an unexpanded stent in a "rolled out" state, depicted as if the stent were cut in the longitudinal direction and rolled out flat such that the entire circumference of the stent may be viewed flat.

FIG. 6 is a side view of a stent 600 in an unexpanded state. More particularly, FIG. 6 is a side view of an unexpanded stent in a "rolled out" state, depicted as if the stent 600 were cut in the longitudinal direction and rolled out flat such that the entire circumference of the stent 600 may be viewed flat.

In some embodiments, a stent 600 may be formed by cutting a pattern, such as that shown in FIG. 6, into a tube of material. In some instances the material may be a memory alloy, and the cutting may be accomplished through use of a laser. The cut tube may then be stretched and expanded. The unexpanded stent of FIG. 6 has many similar features to the other stents discussed herein, though the other stents were depicted in expanded states.

As mentioned in connection with other embodiments, and as illustrated in FIG. 6, a stent 600 may be configured such that strut arms 614 toward the ends 602, 604 of the stent 600 may be longer than strut arms 614 disposed at or near the mid-body 603 of the stent 600.

In the illustrated embodiment, the stent 600 has 11 total rows of annular segments 612. As illustrated, the rows 612 closest to either end are configured to comprise flared portions of an expanded stent. In the illustrated embodiment, the strut arms 614 near the ends 602, 604 of the stent 600 are relatively longer than the strut arms 614 located near the mid-body 603 of the stent 600. A wide variety of strut arm 614 lengths is within the scope of this disclosure. For example, in some instances the strut arm 614 lengths may vary along the length of the stent 600 from strut arm 614 lengths of about 4 mm to about 5.25 mm.

In the illustrated embodiment, the relative length of the strut arms 614 gradually increases beginning at the mid-body 603 of the stent 600 moving toward either end 602, 604. For example, in one embodiment the lengths of the strut arms 614 may be about 4 mm at the mid-body 603 of the stent 600 and gradually increase to about 5.25 mm near the proximal 602 or distal 604 ends of the stent 600. In other embodiments the strut arms 614 may likewise vary from about 4.25 mm to about 5.0 mm, or from about 4.5 mm to about 4.75 mm. In still other embodiments, the stent 600 may be designed such that the strut arm 614 lengths in a particular zone of the stent 600 are constant and gradually change in other zones. For instance, in some embodiments, a relatively long stent may be formed by forming a mid-body 603 section with a constant strut arm 614 length and gradually increasing the strut arm 614 length in flare zones adjacent the ends 602, 604 of the stent 600. Numerous stent lengths are within the scope of this disclosure, including, for example, stents from about 70 mm to about 150 mm in length, including stents from about 100 mm to about 120 mm in length.

Figure 6A:
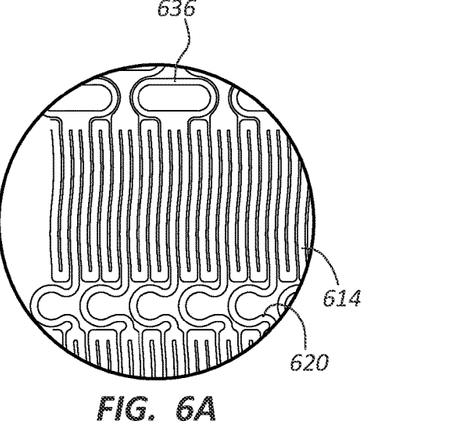
FIG. 6A is a close up view of the stent of FIG. 6.
Figure 6B:
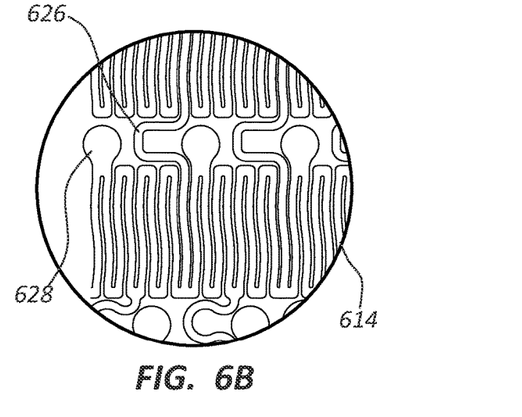
FIG. 6B is a second close up view of the stent of FIG. 6.
Figure 6C:
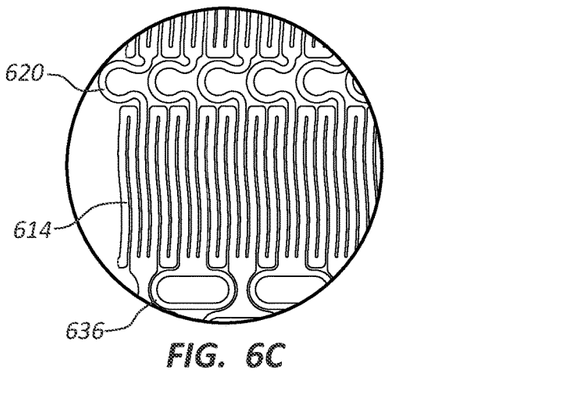
FIG. 6C is a third close up view of the stent of FIG. 6.

FIGS. 6A-6C are detail views of portions of the unexpanded stent of FIG. 6. These figures show the relative position of the strut arms 614, suture threading eyelets 636, connectors 620, and anti-migration portions 628 when the stent 600 is in an unexpanded state.

As shown in FIGS. 6 and 6A the relative size of the suture threading eyelets 636 may be related to the total number of eyelets and the diameter of the tube of material from which the stent 600 is cut. In some embodiments, the eyelets may be shaped with the maximum elongation in the circumferential direction allowed by the number of eyelets 636 and the circumference of the tube.

In the embodiment of FIG. 6, the stent 600 is configured such that there are ten connectors 620 coupling the most proximal annular segment 612h to the adjacent annular segment and ten connectors 620 coupling the most distal annular segment 612i to the adjacent annular segment. All other annular segments 612 of the illustrated embodiment are coupled by five total connectors 620. In other embodiments, the annular segments 612 near the ends 602, 604 of the stent 600 may be coupled with more or fewer connectors 620, for example from eight to twelve connectors 620 in some instances, while the other annular segments 612 may be coupled by four to six connectors in some instances. In some embodiments, a relatively greater number of connectors 620 coupled to the annular segments 612 nearest the ends 602, 604 may limit elongation of the stent 600 when an axial force is applied to the stent 600. Limiting elongation may be desirable in certain instances, particularly instances where the stent 600 is designed to neck down with minimal elongation. Additionally, just as connector 620 length and shape may be adjusted to control properties of the stent 600, the number of connectors 620 utilized to couple adjacent annular segments 612 may be adjusted and vary along the length of the stent 600.

Numerous sizes and configurations of stents are within the scope of this disclosure. By way of example, and not limitation, in addition to esophageal stents, the current disclosure is applicable to biliary stents, bronchial stents, tracheal stents, and colonic/duodenal stents. In some embodiments this disclosure may be used with such stents in the following sizes and dimensions. Biliary stents: mid-body diameters from about 6 mm to about 11 mm including diameters of about 8 mm to about 10 mm; flare sections configured to expand from about 0.5 mm to about 2 mm in diameter greater than the mid-body diameter of the stent; and lengths of from about 40 mm to about 100 mm, including lengths from about 60 mm to about 80 mm. Bronchial stents: mid-body diameters from about 8 mm to about 16 mm including diameters of about 10 mm to about 14 mm; flare sections configured to expand from about 0.5 mm to about 2.5 mm in diameter greater than the mid-body diameter of the stent; and lengths of from about 15 mm to about 40 mm, including lengths from about 20 mm to about 30 mm. Tracheal stents: mid-body diameters from about 16 mm to about 22 mm including diameters of about 18 mm to about 20 mm; flare sections configured to expand from about 0.5 mm to about 2.5 mm in diameter greater than the mid-body diameter of the stent; and lengths of from about 40 mm to about 80 mm, including lengths of about 60 mm. Colonic/duodenal stents: mid-body diameters from about 20 mm to about 25 mm including diameters of about 22 mm; flare sections configured to expand from about 0 mm to about 5 mm in diameter greater than the mid-body diameter of the stent, including embodiments configured with a 5 mm flare on the proximal end of the stent and no flare on the distal; and lengths of from about 50 mm to about 140 mm, including lengths from about 70 mm to about 120 mm. As provided above, any of these stents may include any combination of features disclosed herein.

Figure 7:
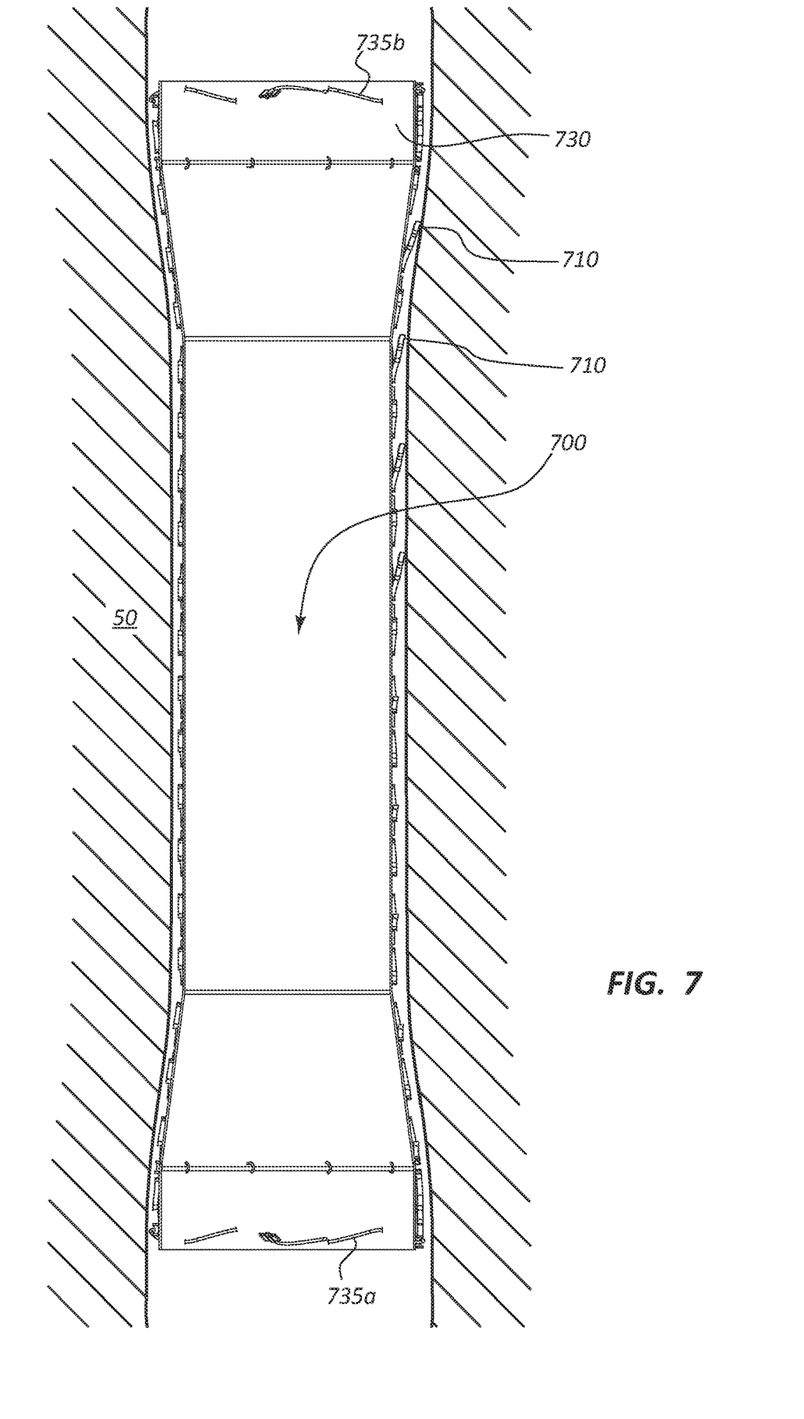
FIG. 7 is a cross-sectional view of a stent disposed within a body lumen.

FIG. 7 is a cross-sectional view of a stent 700 deployed within a body lumen 50. The stent comprises a scaffolding structure 710, a covering 730, and two sutures 735a, 735b.

The examples and embodiments disclosed herein are to be construed as merely illustrative and exemplary, and not a limitation of the scope of the present disclosure in any way. It will be apparent to those having skill in the art that changes may be made to the details of the above-described embodiments without departing from the underlying principles of the disclosure herein. It is intended that the scope of the invention be defined by the claims appended hereto and their equivalents.

The invention claimed is:

1. An implantable device having a cylindrical shape, configured to be disposed within a body lumen, the device comprising:
   a proximal end, a distal end, and a midsection;
   a scaffolding of struts, comprising:
      a plurality of annular segments arranged in alignment along a longitudinal direction of the cylindrical shape of the implantable device, each annular segment comprising a plurality of interconnected arms disposed on a circumference of the cylindrical shape of the implantable device, each arm of the plurality of interconnected arms interconnected with a first adjacent arm at an angle to form an apex and interconnected with a second adjacent arm at the angle to form an oppositely directed apex, wherein the plurality of interconnected arms in the proximal end are circumferentially aligned with each other, and the plurality of interconnected arms in the distal end are circumferentially aligned with each other and are offset from the plurality of interconnected arms in the proximal end;

a plurality of anti-migration portions each comprising a solid rounded blunt tip, each anti-migration portion coupled to and extending from an apex at a connection of two interconnected arms of the plurality of interconnected arms of the plurality of annular segments of the midsection of the implantable device, wherein each annular segment of the midsection of the implantable device comprises an outside diameter, wherein the two interconnected arms and the solid rounded blunt tip of each given anti-migration portion extend together radially outward relative to the outside diameter of the annular segment of the midsection of the implantable device to which the given anti-migration portion is coupled;

a plurality of connectors extending between and interconnecting adjacent annular segments of the plurality of annular segments, the plurality of connectors arranged in an alternating pattern, wherein a given connector of the plurality of connectors that extends in a first longitudinal direction from a given annular segment, of the plurality of annular segments, to a first adjacent annular segment is offset in a circumferential direction of the cylindrical shape from all connectors of the plurality of connectors extending in a second longitudinal direction, opposite the first longitudinal direction, from the given annular segment to a second adjacent annular segment, such that a gap is defined directly in the longitudinal direction to the given connector between the given annular segment and the second adjacent annular segment and between connectors of the plurality of connectors interconnecting the given annular segment and the second adjacent annular segment; and a first plurality of eyelets each coupled to an end annular segment disposed at the proximal end of the implantable device, each eyelet comprising an eyelet body coupled to an end side of, and extending circumferentially from, an apex at a connection of two interconnected arms of the plurality of interconnected arms of the end annular segment, each eyelet body defining an eyelet opening therethrough that is elongated in the circumferential direction of the cylindrical shape such that a maximum length of the eyelet opening is at least twice as long as a maximum width of the eyelet opening;

a polymeric cover comprising a first layer of silicone, the cover applied to and between the scaffolding of struts, the cover defining an interior region within the scaffolding; and a suture threaded through the eyelet openings of the first plurality of eyelets, wherein at least one set of interconnected arms comprises a straight arm and a curved arm that comprises an inflection point.

2. The implantable device of claim 1, wherein the angle formed by the interconnection of adjacent arms of an annular segment is 45 degrees.

3. The implantable device of claim 1, wherein the scaffolding of struts is comprised of a memory alloy with a thickness of 0.30 mm to 0.6 mm.

4. The implantable device of claim 3, wherein the scaffolding of struts comprises an integral frame of nickel-titanium alloy.

5. The implantable device of claim 1, further comprising a second plurality of eyelets each coupled to a second end annular segment disposed at the distal end of the implantable device opposite the proximal end, each eyelet of the second plurality of eyelets comprising an eyelet body coupled to an end side of, and extending circumferentially from, an apex at a connection of two interconnected arms of the plurality of interconnected arms of the second end annular segment, each eyelet body defining an eyelet opening therethrough that is elongated in the circumferential direction of the cylindrical shape, the eyelets configured to receive the suture.

6. The implantable device of claim 1, wherein strut arms disposed adjacent the proximal and the distal ends are longer than strut arms disposed at the midsection.

7. The implantable device of claim 6, wherein connectors disposed adjacent to the proximal and the distal ends are longer than connectors disposed at the midsection.

8. The implantable device of claim 1, wherein the polymeric cover further comprises a second layer.

9. The implantable device of claim 1, wherein one or more of the connectors comprise a preformed omega shaped portion, wherein a curved member of the omega shaped portion folds back upon legs of the omega shaped portion.

10. The implantable device of claim 1, wherein the plurality of annular segments is configured to reduce in diameter in response to an axial force applied to the implantable device.

11. The implantable device of claim 1, wherein an inside radius at the angle formed by adjacent arms is from 15 microns to 95 microns.

12. The implantable device of claim 1, wherein the device has a longitudinal length from 70 mm to 150 mm.

13. The implantable device of claim 1, wherein the device has a diameter of 12 mm to 25 mm.

14. An implantable device having a cylindrical shape, configured to be disposed within a body lumen, the device comprising:

a scaffolding of struts, comprising:

a plurality of annular segments arranged in alignment along a longitudinal direction of the cylindrical shape of the implantable device, each annular segment comprising a plurality of interconnected arms disposed on a circumference of the cylindrical shape of the implantable device, each arm of the plurality of interconnected arms interconnected with a first adjacent arm at an angle from 30 degrees to 60 degrees to form an apex and interconnected with a second adjacent arm at the angle to form an opposing apex, wherein the plurality of interconnected arms in a proximal end of the implantable device are circumferentially aligned with each other, and the plurality of interconnected arms in a distal end of the implantable device are circumferentially aligned with each other and are offset from the plurality of interconnected arms in the proximal end;

a plurality of anti-migration portions each comprising a solid rounded blunt tip, the solid rounded blunt tip portion lacking an opening, each anti-migration portion coupled to and extending from an apex at a connection of two interconnected arms of the plurality of interconnected arms of the plurality of annular segments, wherein each annular segment comprises an outside diameter, wherein the two interconnected arms and the solid rounded blunt tip of each given anti-migration portion extend together radially outward from the outside diameter of the annular segment to which the given anti-migration portion is coupled;

a plurality of connectors extending between and interconnecting adjacent annular segments of the plurality of annular segments, the plurality of connectors arranged in an alternating pattern, wherein a given connector of the plurality of connectors that extends in a first longitudinal direction from a given annular segment to a first adjacent annular segment is offset in a circumferential direction of the cylindrical shape from all connectors of the plurality of connectors extending in a second longitudinal direction, opposite the first longitudinal direction, from the given annular segment to a second adjacent annular segment such that, for each annular segment, all connectors extending in the first longitudinal direction are offset in the circumferential direction of the cylindrical shape from all connectors on the same annular segment that extend in the second longitudinal direction;

a first plurality of eyelets each coupled to a first end annular segment disposed at a first longitudinal end of the cylindrical shape, each eyelet comprising an eyelet body coupled to an end side of, and extending circumferentially from, an apex at a connection of two interconnected arms of the plurality of interconnected arms of the first end annular segment, each eyelet body defining an eyelet opening therethrough that is elongated in the circumferential direction of the cylindrical shape such that a major axis of the eyelet opening is longer than a minor axis of the eyelet opening; and a second plurality of eyelets each coupled to a second end annular segment disposed at a second longitudinal end of the cylindrical shape opposite the first longitudinal end, each eyelet comprising an eyelet body coupled to an end side of, and extending circumferentially from, an apex at a connection of two interconnected arms of the plurality of interconnected arms of the second end annular segment, each eyelet body defining an eyelet opening therethrough that is elongated in the circumferential direction of the cylindrical shape such that a major axis of the eyelet opening is longer than a minor axis of the eyelet opening;

a first suture threaded through the eyelet openings of the first plurality of eyelets;

a second suture threaded through the eyelet openings of the second plurality of eyelets; and a cover coupled to the scaffolding of struts, the cover comprising a silicone layer, wherein one or more of the plurality of annular segments is configured to reduce in diameter in response to an axial force applied to the implantable device, wherein one or more of the connectors comprise a preformed omega shaped portion, wherein a curved member of the omega shaped portion folds back upon legs of the omega shaped portion, and wherein at least one set of interconnected arms comprises a straight arm and a curved arm that comprises an inflection point.

15. The implantable device of claim 14, wherein the scaffolding of struts is comprised of a memory alloy.

16. The implantable device of claim 15, wherein the scaffolding of struts has a thickness of from 0.30 mm to 0.60 mm.

17. The implantable device of claim 14, wherein an inside radius of the angle formed by adjacent arms is from 15 microns to 95 microns.

18. The implantable device of claim 14, wherein the cover further comprises a second layer.

19. A method of treating a stricture or fistula in a body lumen comprising:
obtaining the implantable device of claim 1; and
deploying the implantable device within an esophagus of a patient.

20. The method of claim 19, further comprising decreasing the diameter of the plurality of annular segments of the implantable device by applying an axial force to the implantable device.

* * * * *